(12) United States Patent
Alexandre et al.

(10) Patent No.: US 6,942,645 B2
(45) Date of Patent: Sep. 13, 2005

(54) NEEDLELESS SYRINGE WITH TWO INJECTION SPEED LEVELS

(75) Inventors: Patrick Alexandre, Gray (FR); Bernard Brouquieres, Toulon (FR); Philippe Gautier, Le Plessis Pate (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 511 days.

(21) Appl. No.: 10/182,901

(22) PCT Filed: Feb. 23, 2001

(86) PCT No.: PCT/FR01/00536
§ 371 (c)(1),
(2), (4) Date: Aug. 2, 2002

(87) PCT Pub. No.: WO01/64269
PCT Pub. Date: Sep. 7, 2001

(65) Prior Publication Data
US 2003/0014006 A1 Jan. 16, 2003

(30) Foreign Application Priority Data
Mar. 1, 2000 (FR) .............................. 00 02633

(51) Int. Cl.[7] .............................. A61M 5/178
(52) U.S. Cl. .............................. 604/168; 604/69; 604/72
(58) Field of Search .............................. 604/68–72, 131, 604/140, 141, 143, 145, 146, 147, 218

(56) References Cited
U.S. PATENT DOCUMENTS

| | | | |
|---|---|---|---|
| 2,704,543 A | 3/1955 | Scherer | |
| 3,335,722 A | 8/1967 | Lowry et al. | |
| 3,605,744 A | 9/1971 | Dwyer | |
| 3,802,430 A | * 4/1974 | Schwebel et al. | 604/69 |
| 4,124,024 A | * 11/1978 | Schwebel et al. | 604/69 |
| 4,447,225 A | 5/1984 | Taff et al. | |
| 5,520,639 A | 5/1996 | Peterson et al. | |
| 6,623,446 B1 | * 9/2003 | Navelier et al. | 604/68 |
| 6,666,843 B1 | * 12/2003 | Alexandre et al. | 604/69 |
| 6,758,829 B2 | * 7/2004 | Alexandre et al. | 604/69 |
| 2002/0183689 A1 | * 12/2002 | Alexandre et al. | 604/69 |
| 2003/0135155 A1 | * 7/2003 | Alexandre et al. | 604/69 |
| 2003/0149396 A1 | * 8/2003 | Alexandre et al. | 604/68 |
| 2004/0249339 A1 | * 12/2004 | Willis et al. | 604/70 |
| 2005/0010167 A1 | * 1/2005 | Alexandre et al. | 604/69 |

FOREIGN PATENT DOCUMENTS

DE 3405671 A1 8/1985

* cited by examiner

*Primary Examiner*—Sharon Kennedy
(74) *Attorney, Agent, or Firm*—Oliff & Berridge, PLC

(57) ABSTRACT

A needleless syringe for injecting a liquid active principle. The syringe improves bioavailability by providing injection at two speed levels. The syringe includes a reservoir contained between an injector and push means subjected to the action of a gas generator. The push means including an end, directed towards the active principle, which forms a delivery head whereof the cross-section is smaller than the powering head cross-section, and the powering travel in the power cylinder is less than the height of the active principle reservoir.

14 Claims, 3 Drawing Sheets

NEEDLELESS SYRINGE WITH TWO INJECTION SPEED LEVELS

CROSS REFERENCE TO RELATED APPLICATIONS

This is the U.S. National Stage of PCT/FR01/00536, filed Feb. 23, 2001, which claims priority from French Application No. 0002633, filed Mar. 1, 2000, the disclosures of which are incorporated herein in their entireties by reference thereto.

The present invention concerns the field of needleless syringes used for intradermal, subcutaneous or intramuscular injections of liquid active principle for therapeutic use in human or veterinary medicine.

A needleless syringe is noninvasive by definition: there is no needle passing through the skin in order to bring the active principle to the place where it is to act. For a needleless syringe, it is necessary for the jet of liquid active principle emerging from an orifice or injection conduit to pierce the skin and penetrate to a greater or lesser depth depending on the type of injection desired: to do so, the jet must have a high speed. If the jet is too slow, there is no perforation of the skin, the liquid spreads across the surface of the skin, and it is lost because it produces no therapeutic effect.

However, once the liquid has pierced the skin and reached the desired depth, the speed of the jet can be lower in order to ensure the passage and diffusion, into the skin, of the liquid active principle remaining to be injected.

To ensure good bioavailability of the active principle, it is therefore desirable to have a high speed for the jet of liquid at the start of injection, then a lower speed to ensure the passage of the remaining liquid. These two speed regimes correspond, in the liquid, to high and then lower injection pressures.

The patent U.S. Pat. No. 2,704,543 deals with this problem and, in order to solve it, proposes a thrust means formed by two concentric pistons which act on a deformable obturator permitting expulsion of the liquid. The internal piston, of small cross section, initially acts alone on the deformable obturator and produces a high pressure of injection, then the two concentric pistons are displaced simultaneously in order to reduce the injection pressure since the effective cross section of thrust is increased while the thrust force acting on the two pistons remains the same as that acting on a single piston. This force is produced by the release of a compressed spring.

The patent U.S. Pat. No. 3,335,722 describes a needleless syringe with a gas generator acting on a thrust means formed by a single piston whose end directed toward the active principle is staged. This piston acts on a deformable obturator permitting complete expulsion of the liquid contained in the reservoir, the variation in injection pressure is obtained solely by controlling the flow rate of gas generated and by increasing the free volume upstream of the piston, the effective cross section of the piston being constant.

The syringes proposed in these patents do not permit control of the two pressure stages, in particular the duration of the initial pressure stage is very difficult to regulate. These syringes moreover use a deformable obturator of complex geometry for complete expulsion of the active principle.

Moreover, these syringes are designed to be used several times and comprise several ancillary devices necessary for recharging with active principle and for reactivating the motors.

The object of the present invention is to propose simple syringes with which it is possible to obtain two stages of pressure and speed of injection of a predetermined level and duration. These syringes could be discarded after use.

The present invention concerns a needleless syringe for injection of a liquid active principle contained in a reservoir situated between, on the one hand, an injector comprising at least one injection conduit, and, on the other hand, a thrust means subjected to the action of a gas generator, said thrust means comprising an end which is directed toward the active principle and constitutes a delivery head whose cross section is equal to the cross section of the reservoir; said syringe is characterized in that the delivery head directed toward the active principle is formed as one piece, and in that the opposite end of the thrust means directed toward the gas generator has a drive head whose cross section is greater than the cross section of the delivery head, the drive travel of the drive head in its drive cylinder being less than the height of the reservoir of active principle.

Along this drive travel, the force acting on the thrust means is the resultant of the pressure exerted on the large cross section of the drive head: the pressure transmitted to the liquid is great and the injection speed is therefore high. After this drive travel, the drive head ceases to be active, the resulting force on the thrust means is the resultant of the pressure exerted on a smaller cross section: that of the reservoir; the pressure in the liquid is then lower, as is the speed of injection of the liquid.

In this invention, liquid active principle will be understood essentially as a more or less viscous liquid, or a mixture of liquids, or a gel. The active principle will be able to be a solid dissolved in a suitable solvent for injection. The active principle will be able to be a solid in the form of a powder in more or less concentrated suspension in a suitable liquid. The granulometry of the solid active principle must be adapted, as must the shape of the conduit, to avoid blockages.

The effective drive travel of the drive head is less than the height of the reservoir of active principle. This effective drive travel is advantageously less than 0.6 times the height of the reservoir and preferably 0.2 times this height.

The drive head and the delivery head advantageously belong respectively to two superposed pistons. The one on the upstream side will be called the upper piston; the other, on the downstream side, toward the reservoir of liquid, will be called the lower piston. These pistons comprise sealing devices such as joints or lips which permit their displacement in appropriate cylindrical chambers: drive chamber for the drive head, and reservoir for the delivery head.

The ratio of the cross sections of the drive head and of the delivery head is advantageously greater than or equal to 1.1. This ratio is preferably between 1.2 and 8 and is advantageously between 2 and 6.

The choice of the drive travel in relation to the height of the reservoir, and the choice of the ratio of the cross sections of the drive head and delivery head, make it possible to control the level and duration of the pressures and consequently the conditions of injection of the liquid active principle, in particular the injection speeds.

In a first embodiment of the syringe according to the invention, the drive head is formed by the engagement of an annular upper piston on an upstream rod integral with a lower piston comprising the delivery head. This engagement is a sliding cylindrical engagement or a conical engagement. It is leaktight. The pressure of the gases is exerted on a large surface: the resultant is considerable. The pressure transmitted to the liquid is great and the speed of injection is high.

In this embodiment, the device limiting the drive travel of the drive head is an abutment at the downstream bottom of the drive cylinder. This abutment arrests the annular upper piston. The gases act on the upstream rod of the lower piston and push it. In this displacement, when the sealing between the annular piston and the upstream rod is rendered inoperative by the displacement of said upstream rod, the pressure of the gases is exerted on a cross section equal to that of the reservoir, the resultant of the pressure forces is smaller than before, and the pressure transmitted to the liquid is lower, as is the speed.

In a second embodiment of the syringe, the drive head is the upstream face of a solid upper piston, and the delivery head is the downstream face of a solid lower piston. More precisely, the upstream face of the upper piston of large cross section will be the drive head. The downstream face of the lower piston, of a cross section smaller than or equal to that of the reservoir, will be the delivery head.

In a first variant of this embodiment, the two pistons are separated by a distance D. A protuberance formed integrally on one of the pistons permits determination of this distance D. The upper piston comes into contact with the lower piston after having been displaced by this distance D and there is a shock effect. To remain within the context of the invention, this distance D must be less than the drive travel of the drive head.

In a second variant, the two pistons are in contact: this is in fact the case when the distance D is zero.

For these two variants, the device limiting the drive travel of the drive head is an expansion chamber forming a continuation of the drive cylinder. This expansion chamber is formed by a widening of the drive cylinder, either by an increase in diameter or by a set of lateral grooves which will allow the gases to pass around the drive head and its sealing device so that the upper piston is no longer subjected to a resultant force on account of the pressure and so that the gases act on the solid lower piston on a cross section equal to that of the reservoir.

In these variants, when the solid upper piston comprising the drive head is in the expansion chamber, it ceases to drive and, at the end of its travel, it comes to bear on a surface comprising gas passages so that said gases act on the lower piston.

In a third embodiment of the needleless syringe according to the invention, the thrust means is a single staged piston whose upstream face belongs to the drive head of large cross section and whose downstream face belongs to the delivery head of smaller cross section. This is the particular case when the two aforementioned pistons are integral.

In this embodiment, the device limiting the drive travel of the drive head is an expansion chamber forming a continuation of the drive cylinder. This expansion chamber is designed in the same way as before, for example by a widening of the drive cylinder, either by increasing the diameter or by a set of longitudinal and lateral grooves which will allow the gas to pass around the drive head so that the gases act on a cross section equivalent to that of the delivery head. In this embodiment, the expansion chamber must be sufficiently long so that the piston is displaced until it comes into abutment on the upstream face of the injector in order to effect injection of all of the liquid contained in the reservoir.

In this invention, the thrust means, in its different embodiments, is displaced by the gases from a gas generator. These gases can be generated by a chemical reaction or by a sudden release of a reserve of compressed gas.

However, the gas generator is preferably a pyrotechnic generator. This type of generator is preferred for its power, its compactness and its reliability, permitting, in the case of prefilled syringes, conceivable shelf lives which are limited only by the conservation times of the active principle.

The present invention solves the problem posed, namely that of being able to easily predetermine the two levels of injection speed and their duration.

The present invention has the advantage of distinction, within the device, of two parts. A pharmaceutical part comprising the body and the reservoir with a downstream injector and an upstream piston: this subassembly can be produced under pharmaceutical industry conditions, especially as regards sterilization and asepsis. This subassembly will be made integral with the rest of the syringe, whose elements have been put together elsewhere under conditions which are less stringent than those associated with the pharmaceutical industry.

The invention is set out above in detail with reference to figures which show different specific embodiments of the invention.

FIG. 1 shows diagrammatically, and in partial longitudinal section, a first embodiment of a needleless syringe according to the invention before use. The syringe is shown vertically, the injector at its downstream end directed downward.

Figure 1:
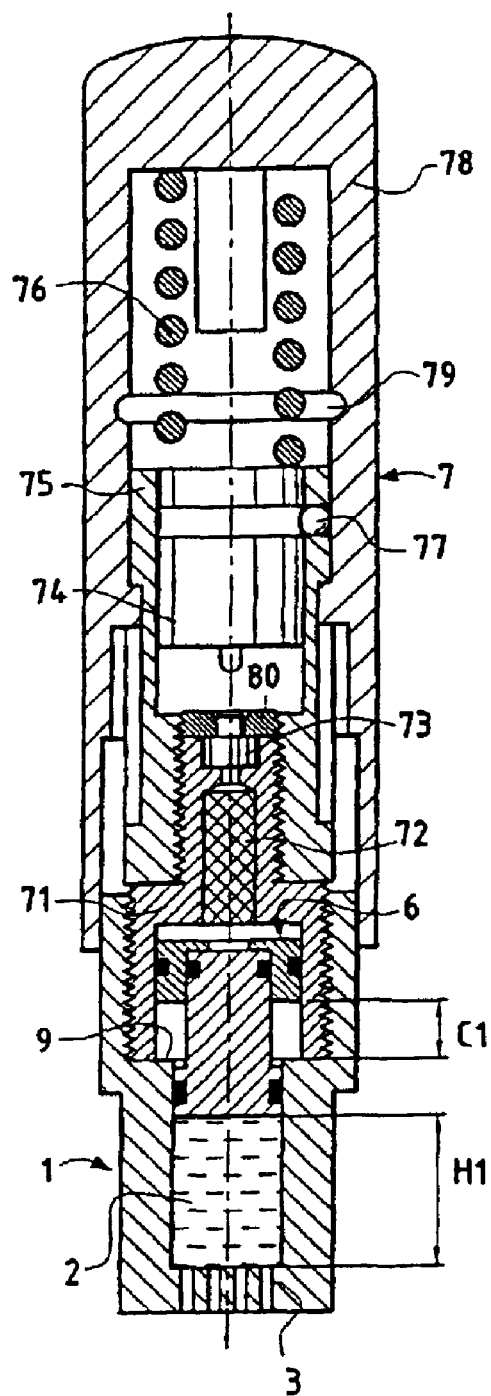
FIG. 1 shows a longitudinal section through a syringe according to a first embodiment.

Starting from the top, this syringe comprises a gas generator 7, which will be described in more detail later. This gas generator is fixed with its body 71 on the reservoir 2 of the syringe. An annular piston 16 which is an element of the drive head 6 is mounted by sliding cylindrical engagement on the upstream end or upstream rod 5 of a second piston whose opposite downstream end is the delivery head 4, and the bearing of the annular piston on the delivery piston is provided for by a suitably dimensioned shoulder. The engagement of the two pistons is rendered leaktight by at least one O-ring seal or any other equivalent means. The annular piston 16 is of large cross section in relation to the piston carrying the delivery head. These pistons comprise O-ring seals or equivalent means to render them leaktight with respect to their displacement chambers: the drive cylinder 10 and the reservoir 2.

We will now describe the main elements of the gas generator 7, which in this example is pyrotechnic. It comprises in the body 71, above the piston comprising the drive head 6, a pyrotechnic charge 72 whose combustion is initiated by a primer 73 impacted by a striker 74; this striker is not shown in cross section, but viewed from the side. The primer 73 is accommodated in a primer holder. In the initial position, the striker 74 is retained in the striker guide 75, screwed integrally to the body 71, via at least one ball, such as the ball 77, which is partially engaged in a groove of the striker. The percussion device comprises a pusher 78 with a groove 79 and an inner spring 76.

The pusher 78 slides on the outside of the striker guide 75 and it is retained by studs which move in lateral grooves. This pusher 78 is in this case the triggering member.

Of course, in order to initiate the combustion of the pyrotechnic charge 72, it is possible, without departing from the scope of the invention, to use initiating devices other than the striker device described here. Without going into details, and without wishing to be exhaustive, we will cite, by way of example, initiating devices with an electric battery or piezoelectric initiating devices.

If appropriate, the pyrotechnic gas generator can be replaced by a gas generator formed by a compressed gas reservoir which is closed by a quick-opening valve. The triggering member will open said valve, and the compressed gases of the reservoir will expand and act on the thrust means.

In this FIG. 1, the syringe is ready for use when the injector is bearing on the skin of the subject to be treated (not shown). The operator presses, with his thumb, on the pusher 78 which moves downward and compresses the spring 76. The pusher is displaced until the groove 79 arrives at the level of the groove of the striker 74, the balls, such as the ball 77, retaining the striker 74 pass into the groove 79 and release the striker which will violently impact the primer 73, the initiation of which ignites the pyrotechnic charge 72. The striker bearing on the primer holder 80 provides sealing: the combustion gases do not rise toward the pusher 78.

During a first phase of operation, the gases from the generator 7 act on the large upstream surface of the annular piston 16 whose central opening is closed off tight by the upstream end of the rod 5 of the piston bearing the delivery head 4. Along the travel $C_1$, the two pistons are displaced jointly, the resultant force being exerted on the thrust means is considerable, the pressure transmitted to the liquid via the delivery head 4 is great: the multiplied effect on the pressure is in first approximation linked to the ratio of the cross sections. The liquid active principle will leave the conduits of the injector 3 at great speed and efficiently pierce and penetrate into the skin of the subject to be treated. The drive travel $C_1$ of the drive head 6 in its drive cylinder 10 is less than the height $H_1$ of the reservoir.

Thereafter, during the displacement of the two pistons, the annular piston of large cross section comes into abutment on the base 9 of the chamber formed by the drive cylinder 10, the annular piston is blocked on this bottom 9. The gases act on the upstream end 5 of the other piston which will continue to move under the effect of a reduced force until the seal no longer provides any sealing, whereas the effective cross section of the piston comprising the delivery head 4 is equal to the cross section of the reservoir 2, which cross section is smaller than the effective cross section of the first phase. The injection pressure is lower, as is the speed of the jet of liquid.

To reduce to a minimum the transitory phase upon disengagement of the two pistons, it is preferable, on the one hand, that the cross section of the upstream part 5 is very similar to that of the delivery head, and, on the other hand, that the opening of the annular piston is as large as possible while at the same time providing a shoulder and a suitable bearing of the annular piston on the upstream part; in this figure, for greater clarity, the size differences have been accentuated.

This reduction of the transitory phase can also be obtained by using an engagement with a conical surface between the annular piston 16 and the upstream rod of the delivery piston. If appropriate, a vent formed through the downstream part 9 and the body 71 for the purpose of evacuating the compressed air between the annular piston 16 and the upstream rod 5 of the delivery piston contributes to reducing the transitory phase.

Figure 2:
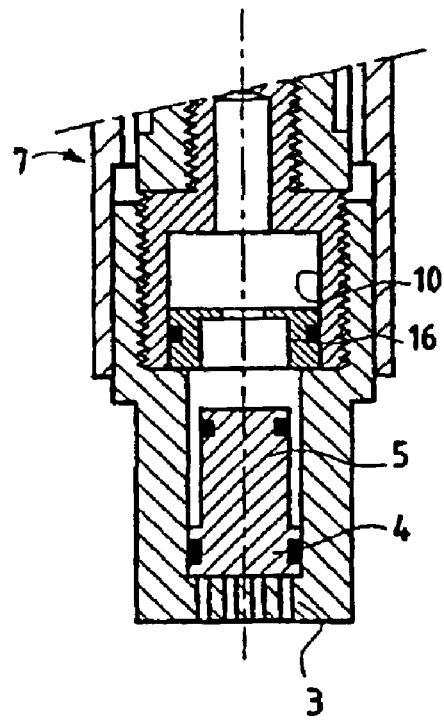
FIG. 2 shows, in a partial view, the position of the pistons after functioning.

FIG. 2 shows, in partial cross section, the downstream part of the syringe at the end of injection. The annular piston 16 is in abutment on the bottom 9 of its drive chamber. The other piston comprising the delivery head is displaced until it comes into abutment on the upstream inner face of the injector 3.

Figure 4:
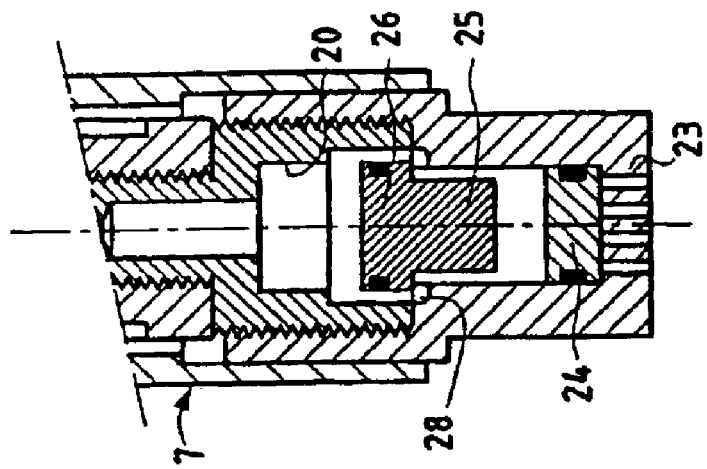
FIGS. 3 and 4 show, in partial views, the pistons in the initial position and in the final position, respectively, for a syringe according to the invention comprising two separate solid pistons.
Figure 3:
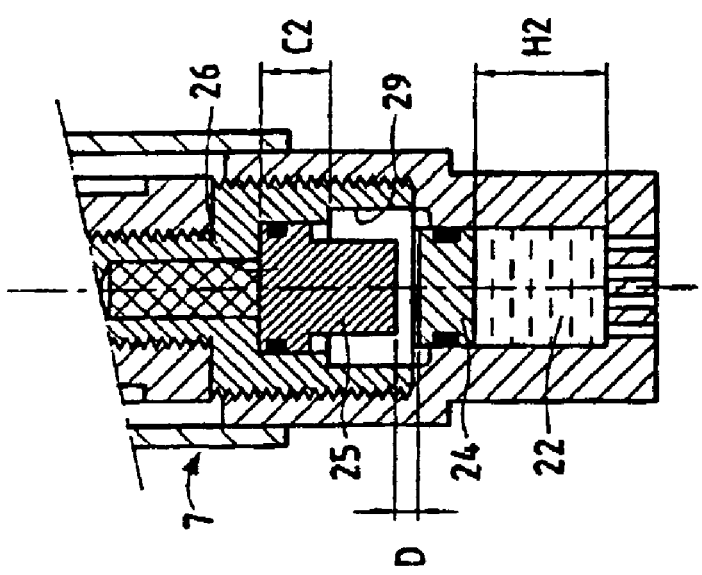

A second embodiment of the invention is shown in FIGS. 3 and 4. These figures show, respectively, the initial state and the final state of the downstream part of the syringe. The drive means is of the type described, by way of example, in FIG. 1, and will continue to be designated by reference number 7.

FIG. 3 shows the initial configuration of this embodiment. The piston bearing the drive head 26 of large cross section is a solid piston, it slides in a drive chamber 20. The downstream face of the piston bearing the drive head comprises a protuberance 25 separated by a distance D from the upstream face of the piston bearing the delivery head 24 which closes the reservoir of liquid. When the functioning of the gas generator is initiated, the gases push the drive head 26 with great force (pressure exerted on a large surface area), the drive piston 26 having traveled the distance D impacts the delivery piston 24 and transmits this great force to it until the drive piston 26 disengages in the expansion chamber 29. The drive travel $C_2$ of the drive head 26 in its drive cylinder 20 is less than the height $H_2$ of the reservoir. This expansion chamber is in this example a chamber with a diameter greater than that of the drive cross section 20 and the gases can circulate around the drive head 26 of large cross section, the resultant force on the pistons 26 and 24 is that corresponding to the pressure of the gases exerted on a surface equal to the cross section of the piston carrying the delivery head 24.

This force is lower and the pressure in the liquid is lower. The delivery piston 24 continues its displacement until all the liquid is ejected from the reservoir. The drive piston 26 is arrested on a surface 28 permitting passage of the gases so that these act on the delivery piston. The surface 28 is, for example, a set of ribs in the downstream part of the chamber 29.

FIG. 4 shows the device in its final state. The drive head 26 has disengaged in the expansion chamber 29, it is arrested on the surface 28 permitting passage of the gases. The delivery piston 24 continued its displacement until it arrives in abutment on the upstream face of the injector 23.

Figure 5:
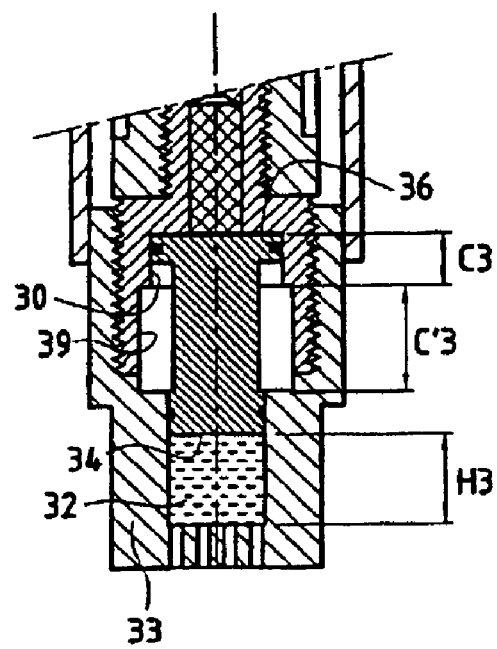
FIG. 5 shows, in a partial view, an embodiment with a single staged piston in its initial position.

Finally, a third embodiment of the invention is shown in FIG. 5. It shows the downstream part of the syringe with a single piston in the initial position.

In this embodiment, the thrust means is a single staged piston: its end of large cross section or drive head 36 is directed toward the gas generator 7; its end of small cross section or delivery head 34 bears on the active principle. The end of the drive head 36 is displaced along a travel $C_3$ in a drive cylinder 30 of large cross section, the resultant effective force of which is considerable and the pressure transmitted to the liquid is great. This drive travel C3 is less than the height $H_3$ of the reservoir. This end 36 then disengages in an expansion chamber 39 whose cross section is greater than that of the drive cylinder 30. As before, this greater cross section is realized by the chamber 39 having a diameter greater than that of the drive cylinder 30. As the gases can circulate around the end 36, the resultant of the pressure will be that exerted on a cross section equal to that of the reservoir and of the delivery head 34: the pressure transmitted to the liquid will be lower. The length $C'_3$ of the expansion chamber will be such that the piston continues its displacement until the delivery head 34 arrives in abutment on the upstream face of the injector 33.

Figure 6:
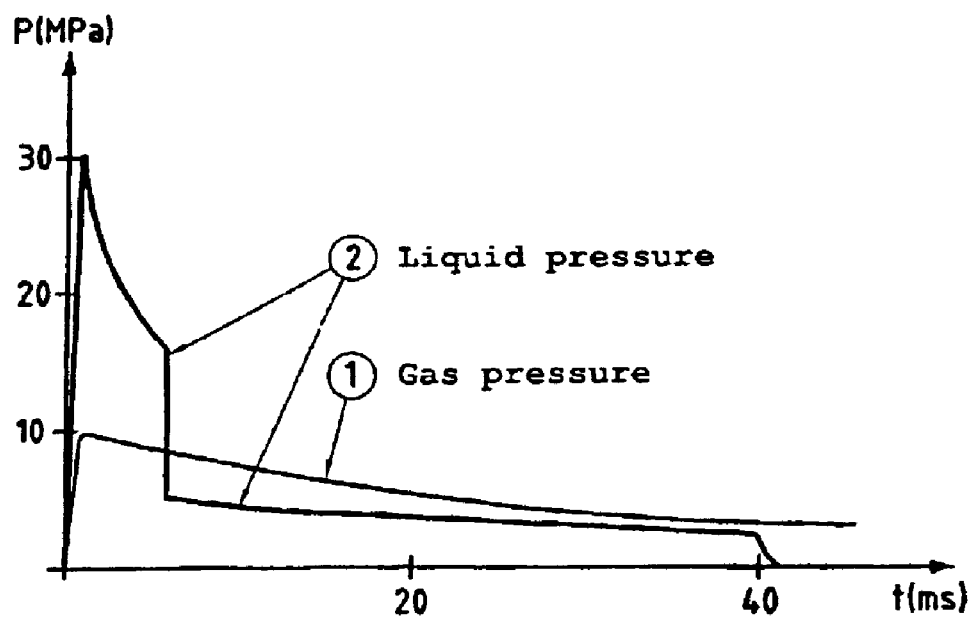
FIG. 6 illustrates an example of pressure curves in the chamber of the gas generator and in the liquid.

For a syringe of the type shown in FIG. 1, and which has been equipped with pressure sensors, FIG. 6 shows, as a function of time, the development of the pressure on the gas generator side (curve 1) and that of the pressure of the liquid (curve 2) on the reservoir side. The gas generator is of the pyrotechnic type and comprises a powder charge based on nitrocellulose. The ratio of the cross sections of the drive and delivery heads is 3.1.

At the start of injection under the effect of the pressure transmitted by the piston to the drive head, the injection pressure of the liquid is almost three times that of the gas. The transition from one regime to the other is very rapid, the instrumentation does not allow it to be followed in a detailed manner. For the second regime, the pressure in the liquid follows that of the gases, except for friction.

What is claimed is:

1. A needleless syringe for injection of a liquid active principle, comprising:

a reservoir;

an injector comprising at least one injection conduit; and a thrust means subjected to the action of a gas generator, the thrust means comprising an end which is directed toward the active principle and constitutes a delivery head having a cross section equal to a cross section of the reservoir, the reservoir situated between the injector and the thrust means, an opposite end of the thrust means is directed toward the gas generator and has a drive head with a cross section greater than the cross section of the delivery head;

wherein the delivery head is formed as one piece, and in that the drive head is active along a drive travel of the drive head in a drive cylinder of the drive head, the drive travel being less than the height of the reservoir of liquid active principle.

2. The needleless syringe as claimed in claim 1, wherein the drive head and the delivery head belong respectively to two superposed pistons.

3. The needleless syringe as claimed in claim 1, wherein the effective drive travel of the drive head is less than 0.6 times the height of the reservoir.

4. The needleless syringe as claimed in claim 1, wherein the drive head is formed by the engagement of an annular upper piston on an upstream rod of a lower piston comprising the delivery head.

5. The needleless syringe as claimed in claim 4, wherein the device limiting the drive travel of the drive head is an abutment at the bottom of a drive cylinder.

6. The needleless syringe as claimed in claim 1, wherein the drive head is the upstream face of a solid upper piston, and in that the delivery head is the downstream face of a solid lower piston.

7. The needleless syringe as claimed in claim 6, wherein the two pistons are separated by a distance.

8. The needleless syringe as claimed in claim 6, wherein the two pistons are in contact.

9. The needleless syringe as claimed in claim 1, wherein the device limiting the drive travel of the drive head is an expansion chamber forming a continuation of the drive cylinder.

10. The needleless syringe as claimed in claim 6, wherein the solid upper piston comprising the drive head comes to bear on a surface comprising gas passages.

11. The needleless syringe as claimed in claim 1, wherein the thrust means is a single staged piston whose upstream face belongs to the drive head and whose downstream face is the delivery head.

12. The needleless syringe as claimed in claim 11, wherein the device limiting the drive travel of the drive head is an expansion chamber having a length that permits contact between the delivery head and the upstream face of the injector.

13. The needleless syringe as claimed in claim 1, wherein the gas generator is a pyrotechnic generator.

14. The needleless syringe as claimed in claim 3, wherein the ratio of the cross sections of the drive head and the delivery head is between 2 and 6.

* * * * *